(12) United States Patent
Fieselmann et al.

(10) Patent No.: US 10,499,875 B2
(45) Date of Patent: Dec. 10, 2019

(54) METHOD FOR ASCERTAINING A TIME FOR A CALIBRATION, X-RAY DEVICE AND COMPUTER PROGRAM

(71) Applicant: SIEMENS HEALTHCARE GMBH, Erlangen (DE)

(72) Inventors: Andreas Fieselmann, Erlangen (DE); Anna Jerebko, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 482 days.

(21) Appl. No.: 15/430,727

(22) Filed: Feb. 13, 2017

(65) Prior Publication Data
US 2017/0231596 A1    Aug. 17, 2017

(30) Foreign Application Priority Data
Feb. 12, 2016  (DE) .......................... 10 2016 202 148

(51) Int. Cl.
*A61B 6/00*   (2006.01)
*A61B 6/04*   (2006.01)

(52) U.S. Cl.
CPC ............ *A61B 6/584* (2013.01); *A61B 6/0407* (2013.01); *A61B 6/4464* (2013.01); *A61B 6/54* (2013.01); *A61B 6/4458* (2013.01); *A61B 6/586* (2013.01)

(58) Field of Classification Search
CPC ...................................................... A61B 6/584
See application file for complete search history.

(56) References Cited

U.S. PATENT DOCUMENTS 9,002,515 B2 *  4/2015  Hornung ............. A61B 6/4441
                                                            378/163
2008/0192884 A1  8/2008  Ritter

FOREIGN PATENT DOCUMENTS

DE    102005005087 A1   8/2006
DE    102009006417 A1   7/2010

OTHER PUBLICATIONS

Strobel, et al., "Improving 3D image quality of x-ray C-arm imaging systems by using properly designed pose Determination systems for calibrating the projection geometry," in [Proc. SPIE Medical Imaging 2003: Physics of Medical Imaging], 5030, 943-954 (2003); 2003.

(Continued)

*Primary Examiner* — Dani Fox
(74) *Attorney, Agent, or Firm* — Laurence Greenberg; Werner Stemer; Ralph Locher

(57) ABSTRACT

A method ascertains a time for a fresh calibration for ascertaining up-to-date calibration parameters of an x-ray device. The x-ray device has multiple degrees of freedom of movement for its recording arrangement. X-ray images of a calibration phantom are recorded for recording positions of the recording arrangement and are evaluated to ascertain the calibration parameters allowing ascertainment of geometry parameters. In multiple operating phases, situated between two calibrations, of a further x-ray device of identical design to the x-ray device, a piece of use information describing the accumulated use of the degrees of freedom of movement during the operating phase and a piece of difference information describing the difference in the calibration parameters between the calibrations delimiting the operating phase, is ascertained and used or determining the time for a fresh calibration.

13 Claims, 2 Drawing Sheets

(56) References Cited

OTHER PUBLICATIONS

Hastie, Tibshirani and Friedman, The Elements of Statistical Learning; Springer-Verlag, New York, 2001 (pp. 42 to 47, pp. 50 to 53, pp. 59 to 65 and pp. 79 to 91); 2001.
Friedman, Jerome H., "Multivariate Adaptive Regression Splines," in: The Annals of Statistics 1991, vol. 19, Nr. 1, pp. 1-141.

* cited by examiner

METHOD FOR ASCERTAINING A TIME FOR A CALIBRATION, X-RAY DEVICE AND COMPUTER PROGRAM

CROSS-REFERENCE TO RELATED APPLICATION

This application claims the priority, under 35 U.S.C. § 119, of German application DE 10 2016 202 148.6, filed Feb. 12, 2016; the prior application is herewith incorporated by reference in its entirety.

BACKGROUND OF THE INVENTION

Field of the Invention

The invention relates to a method for ascertaining a time for a fresh calibration for ascertaining up-to-date calibration parameters of an x-ray device. The x-ray device has multiple degrees of freedom of movement for its recording arrangement containing an x-ray emitter and an x-ray detector. A calibration process involves x-ray images of a calibration phantom being recorded for at least some of the possible recording positions of the recording arrangement and being evaluated to ascertain the calibration parameters allowing ascertainment of geometry parameters, describing the recording geometry, from position data of the recording arrangement that are based on the degrees of freedom of movement. In addition, the invention relates to a control system and a computer program.

The prior art already discloses a multiplicity of x-ray devices, the recording arrangements of which have adjusting devices in multiple degrees of freedom of movement, so that, in particular, it becomes possible to record x-ray images in different recording geometries, particularly using different projection directions. Precise knowledge of the recording geometries that can be set on the basis of the degrees of freedom of movement is necessary particularly when computed tomography methods and/or methods similar to computed tomography are performed, that is to say, in general terms, a plurality of projection images are recorded in different recording geometries, particularly along different projection directions resulting from a recording trajectory, and an, in particular three dimensional, image data record is reconstructed therefrom. Specifically when the projection images are recorded using cone-beam geometry, exact knowledge of the recording geometry is important.

Examples of x-ray devices that do not require a gantry, which usually has small mechanical tolerances, and that nevertheless allow projection images for reconstructing a higher-dimensional image data record and/or a sectional image to be produced along trajectories of the recording arrangement are x-ray devices having a C-arm, on which the x-ray emitter and the x-ray detector are arranged opposite one another, and at least partially robot-arm-based x-ray devices, in which the x-ray emitter and the x-ray detector can each be adjusted robotically in multiple degrees of freedom of movement, for example. An example of the latter type of x-ray devices is the device marketed by Siemens Healthcare GmbH under the name "Multitom Rax", which has ten degrees of freedom of movement. The "Artis Zeego" device, likewise marketed by Siemens Healthcare GmbH, can also be cited.

Specifically in the case of such x-ray devices, which use more complex mechanics, it may happen, over time, that recording geometries differ despite nominally identical set positions of the recording arrangement, that is to say of the x-ray emitter and the x-ray detector. Therefore, such x-ray devices have provision for calibration parameters to be ascertained that allow geometry parameters describing the recording geometry to be derived from position data of the recording arrangement that are based on the degrees of freedom of movement, wherein, besides the position data, an additional reference to a particular trajectory to be traveled along during recording of projection images is possible, since the resultant recording geometries may also be dependent on the trajectory used, particularly the state of movement before a particular imaging position is reached, for example described by the starting point thereof. In order to ascertain the calibration parameters from which the recording geometries can be derived, a calibration measurement is performed by recording x-ray images of a dedicated calibration phantom, particularly along at least some of the conceivable/usable trajectories of the recording arrangement. Such an approach is described by way of example in an article by Strobel et al., entitled: "Improving 3D Image Quality of X-Ray C-Arm Imaging Systems by using Properly Designed Pose Determination Systems for Calibrating the Projection Geometry," in: Proc. SPIE Medical Imaging 2003: Physics of Medical Imaging, 5030, 943-954 (2003). It is assumed that the trajectories or the recording geometries are reproducible for particular nominal position data resulting from the actuation of the adjusting devices at least for an interval of time for which the calibration parameters that have been derived from the x-ray images of the calibration phantom are valid. A calibration phantom can contain, by way of example, a plurality of features in a particular arrangement, for example what are known as metal balls ("beads") of different diameter, so that the present recording geometry can be derived from a recorded two-dimensional x-ray image.

The specific design of the x-ray device, particularly the number and relative configuration of degrees of freedom of movement, has an influence on the number of single scans or x-ray images to be recorded during a calibration. This usually requires fewer calibration scans or single x-ray images to be recorded for C-arm-based x-ray devices, for example, than for robotic multiaxis x-ray devices such as the aforementioned Multitom Rax. For robotic multiaxis x-ray devices, a multiplicity of single x-ray images is needed on the basis of the starting position when travelling along a trajectory.

Ascertainment of the calibration parameters during a calibration is a time consuming process, which means that the frequency of the calibrations should be kept as low as possible. According to the present prior art, calibrations are either performed afresh after a previously stipulated interval of time or when it is known, for example obvious from measurements or consideration of the x-ray device, that the calibration parameters are no longer valid. Unsuitable calibration parameters can lead to poorer image quality, while calibrations performed too frequently entail a high time involvement.

Published, non-prosecuted German patent application DE 10 2005 005 087 A1 relates to a method for correcting unreproducible geometry errors in an x-ray C-arm device. This involves ascertaining a 2D data record adversely affected by an unreproducible geometry error and comparing the 2D data record with the known projection matrices that compensate for reproducible geometry errors in the C-arm device, after which the result of this comparison is used to alter the projection matrices of the scan such that an unreproducible geometry error occurring during the scan is compensated for. As such, it is possible to achieve an increase in the resolution of the 2D data records and accordingly in a 3D reconstruction generated therefrom.

Published, non-prosecuted German patent application DE 10 2009 006 417 A1 discloses a monitoring system for a medical device that contains a robot and an image recording component moved by the robot. The robot has a radiation source mounted on it that has an associated radiation receiver that is not mounted on the medical device but rather is remote therefrom. The impingement location for radiation on the radiation receiver can be compared with a particular prescribed impingement location, with a fault report or an alarm being able to be output in the event of a difference, for example.

SUMMARY OF THE INVENTION

The invention is therefore based on the object of predicting a time for a fresh calibration in order to allow minimization of the time used for the calibration processes at the same time as high-quality calibration parameters are available.

To achieve this object, a method of the type cited at the outset has provision, according to the invention, that in multiple operating phases, situated between two calibrations, of the and/or of at least one x-ray device of identical design to the x-ray device, a piece of use information, containing use data describing the accumulated use of the degrees of freedom of movement during the operating phase and a piece of difference information describing the difference in the calibration parameters between the calibrations delimiting the operating phase, is ascertained. The time for a fresh calibration is determined from a relationship, determined by collective evaluation of all use information, between the use data and the difference information on the basis of the use data recorded since the last calibration.

In particular, the calibration parameters can then be used, as has already been explained by way of introduction, for the reconstruction of an image data record from projection images recorded using the x-ray device in different recording geometries defined along a trajectory of the recording arrangement.

The method according to the invention allows suitable, in particular optimum, times for a fresh calibration to be determined by suitable analysis of the use when viewed together with the alteration that has occurred in the calibration. This therefore first of all involves a plurality of pieces of use information being determined that relate to individual operating phases of at least the x-ray device itself, but preferably of multiple x-ray devices of identical design. In this case, a piece of use information contains use data describing the accumulated use of the degrees of freedom of movement during the operating phase, which use data therefore indicates the extent to which movements along the individual degrees of freedom of movement have been effected by the relevant adjusting devices of the x-ray device. Further, a piece of use information also contains details of how the calibration parameters and/or other variables determined in the course of calibration differ, however. The difference information thus describes the extent to which the calibration has altered between the two individual calibration processes. In this case, it should be noted at this juncture that the calibration parameters can also contain geometry parameters, for example in the form of a projection matrix, that are associated directly with particular projection data (and possibly trajectories); however, it is just as conceivable for the calibration parameters to produce a functional relationship between the position data (and possibly trajectories) and the geometry parameters, particularly projection matrices.

If only a particular minimum number of pieces of use information are available, these can be evaluated in order to produce a relationship, therefore a correlation, between the use data and the difference information. This may be particularly a mathematical relationship, since also ultimately the use data and the difference information are each available as at least one value in the use information. This particular relationship can then be used subsequently to determine, on basis of up-to-date use data recorded since the last calibration, what difference there is predictively from the most recently performed calibration, from which it is in turn possible to derive a suitable time for a fresh calibration.

In this case, as has already been mentioned, it is preferred if use information can be obtained from multiple x-ray devices of identical design in order to be able to determine the relationship in as robust and statistically relevant a manner as possible. The ascertained relationship can then be used on all of these x-ray devices to ascertain an ideal time for a fresh calibration. In principle, however, it is also conceivable for the method to be performed using a single x-ray device, particularly within same.

As has already been mentioned, it is expedient to use the relationship only when a particular base of use information, for example a minimum number of pieces of use information from different operating phases or different x-ray devices, is available. In this regard, a development of the present invention provides that the time is determined on the basis of the use information only when use information is available for a number of operating phases for the or all x-ray devices that exceeds a threshold value, wherein fixed intervals of time are used beforehand for spacing the calibrations. In this case, it should be pointed out that the threshold value can also be adapted dynamically on the basis of a quality value describing the quality of the correlation. Thus, while there is still no reliable relationship available, a fixed interval of time is used to space the calibrations. By way of example, there may initially be provision for a calibration to be performed every four weeks until an adequate database for reliably determining the relationship is available.

The present invention thus allows the intervals between calibrations to be maximized while maintaining a particular minimum quality of the calibration parameters, so that less time per annum can be used for calibrations in total if the calibration is more robust than an average calibration, and a higher image quality can be achieved if the calibration is less robust than an average calibration.

While it is fundamentally conceivable for the use data to relate solely to the number of examinations performed, for example, this is less preferred according to the invention. Instead, storage of the use data in a manner broken down according to degrees of freedom of movement and/or trajectories used for the recording arrangement is preferably used.

A particularly advantageous configuration of the present invention therefore provides that the use data are recorded in a manner resolved according to degrees of freedom of movement and/or trajectories used for the recording arrangement. In a concrete configuration, there may be provision that the use data used are a length of movement along each degree of freedom of movement, and/or use data based on trajectories are taken into consideration in a manner weighted with a length of movement along all degrees of freedom of movement for this trajectory, and/or the trajectories are associated with degrees of freedom of movement information, so that use data based on degrees of freedom of movement are derived from use data based on trajectories. It is particularly preferred in this case if the use data are either based on degrees of freedom of movement or can be based on degrees of freedom of movement. In practice, it has been found that frequent use of some degrees of freedom of movement, for example particular rotational or translational degrees of freedom of movement, can have a greater influence on an alteration of the recording geometries than in the case of other degrees of freedom of movement, which can be taken into consideration in adequate fashion within the context of this configuration. However, a distinction between different trajectories and the weighting thereof can itself also entail advantages, since this allows a more dedicated assessment than if just the number of examinations performed were counted. By way of example, trajectories having a lot of movement or particularly onerous movement processes can be weighted higher than those with less movement involved.

It is expedient, further, if particularly the collection of use information for multiple x-ray devices involves the use information being transmitted from the x-ray device recording it to a central computation device, where at least some of the evaluation is effected, particularly determination of the relationship is affected. This is expedient particularly to the effect that other proposals for applications also exist that are aimed at evaluating use information from x-ray devices, for example for the purpose of ascertaining causes of faults and/or generally for the purpose of improving the x-ray devices in future development. Therefore, the use of a central computation device allows the recorded use information to be used also for purposes other than those described here. In addition, a central computation device allows use information from different x-ray devices of identical design to be collected centrally and evaluated collectively, after which the accordingly determined relationships can be transmitted back to the individual x-ray devices for further use, for example.

It is expedient, further, if the relationship is updated whenever there is a fresh piece of use information available or whenever there is a predetermined number n of pieces of use information available. In particular, it is naturally expedient to store/transmit and use a relevant piece of use information whenever a fresh calibration is performed in order to be able to train the model described by the relationship further. Hence, an up-to-date database is always being used and the quality of the relationship increases constantly.

In a concrete configuration of the invention, there may be provision that the relationship is provided by virtue of training of a mathematical model described by at least one model parameter, particularly by virtue of a fit process. Therefore, an algorithm can be used that uses a mathematical model as a basis for the relationship between the use data and the difference information and ascertains model parameters of this mathematical model. In this case, a large number of methods can be used for fitting mathematical models to continuous variables, for example linear regression, nonlinear regression, regression trees, CHAID, neural networks and the like, reference being made merely by way of example to the standard work by Hastie, Tibshirani and Friedman, "The Elements of Statistical Learning", Springer-Verlag, New York, 2001.

It is particularly preferred, however, if the relationship is ascertained by virtue of a nonparametric multivariate adaptive regression splines method. In this case, advantageously, no assumption is made about a functional relationship between the use data and the difference information; in addition, the method is suitable for highly dimensional problems. The basis of this method is a mathematical model that consists of a weighted sum of basic functions, the basic functions containing a constant 1, hinge functions and products of two or more hinge functions. Their basic functions modulate interactions between two or more variables. For a more exact explanation, reference is made to the article by Jerome H. Friedman, "Multivariate Adaptive Regression Splines", in: The Annals of Statistics 1991, Volume 19, No. 1, pages 1-141.

For the purpose of ascertaining the time for a fresh calibration, there may be concrete provision for the relationship to be used to ascertain a piece of difference information from the use data recorded since the last calibration and for the difference information to be evaluated using a recalibration criterion. This can involve, by way of example, a difference value contained in the predicted difference information and/or derivable therefrom being compared to a threshold value. Once the threshold value for the difference has been reached, a fresh calibration is initiated.

In this case, it should also be noted at this juncture that an embodiment of the present invention can provide for the difference information to be ascertained as a scalar difference value, for example as a sum of the absolute values of differences based on single features of the calibration phantom and/or as a sum of the absolute values of the differences of single calibration parameters. However, it is also conceivable to use a piece of difference information broken down according to different differences.

Particularly in the last case, that is to say in the case of a piece of difference information broken down according to different differences, a particularly preferred configuration of the present invention provides that a piece of predictive difference information ascertained by the relationship from the use data recorded since the last calibration is used for plausibilizing the relationship in the event of a fresh calibration and/or for preadaptation of the calibration parameters and/or restriction of a selection of positions and/or trajectories of the recording arrangement before a fresh calibration, particularly one shifted to a later time. It is therefore possible to predict adapted difference information and hence adapted calibration parameters that are based on the up-to-date calibration parameters and the known movement in the system, that is to say the use data. Such a prediction can be used in the case of a fresh calibration for the purpose of plausibilizing the relationship, so that, by way of example, it is possible to check how accurately the difference information has been predicted by performing a comparison with the actual difference information from the operating phase concluded with the fresh calibration. Further useful applications of such predicted difference information are also conceivable, however. As such, it is possible, particularly in the event of a high level of reliability for the relationship, to perform preadaptation of the calibration parameters based on the predicted difference information, which allows a fresh calibration to be stalled somewhat, since some of the difference effects have already been corrected, of course. Further, there may be provision for the selection of positions and/or trajectories for the recording arrangement to be restricted if the difference information approaches a piece of critical information that would necessitate a fresh calibration. In this case, it is possible, by way of example, to use specifically trajectories and/or positions that result in as small as possible a burden of movement for the x-ray device in the individual degrees of freedom of movement or at least the degrees of freedom of movement affected to the greatest extent, so that this also allows a fresh calibration to be put off in time.

Besides the method, the invention also relates to a control system for at least one x-ray device, containing the x-ray device and a control device designed for performing the method according to the invention. In this case, the control system is preferably provided for multiple x-ray devices of identical design and additionally has a central computation device on which the evaluation of the use information of the individual x-ray devices is effected at least to some extent. In this case, the control device may naturally be distributed in space, so that, for example, ascertainment of the relationship can take place in the central computation device, while use of the relationship for predicting a time for the fresh calibration is affected in the individual x-ray devices, just like ascertainment of the use information (and naturally the calibration itself). All explanations concerning the method according to the invention can be transferred analogously to the control system according to the invention, which can therefore likewise be used to obtain the advantages already cited.

Finally, the invention also relates to a computer program that performs the steps of the method according to the invention when it is executed on a computation device, for example a control device of the control system. The computer program may be stored on at least one electronically readable data storage medium, for example a CD-ROM. In this regard too, the previous explanations continue to apply.

Other features which are considered as characteristic for the invention are set forth in the appended claims.

Although the invention is illustrated and described herein as embodied in a method for ascertaining a time for a calibration, an x-ray device and a computer program, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
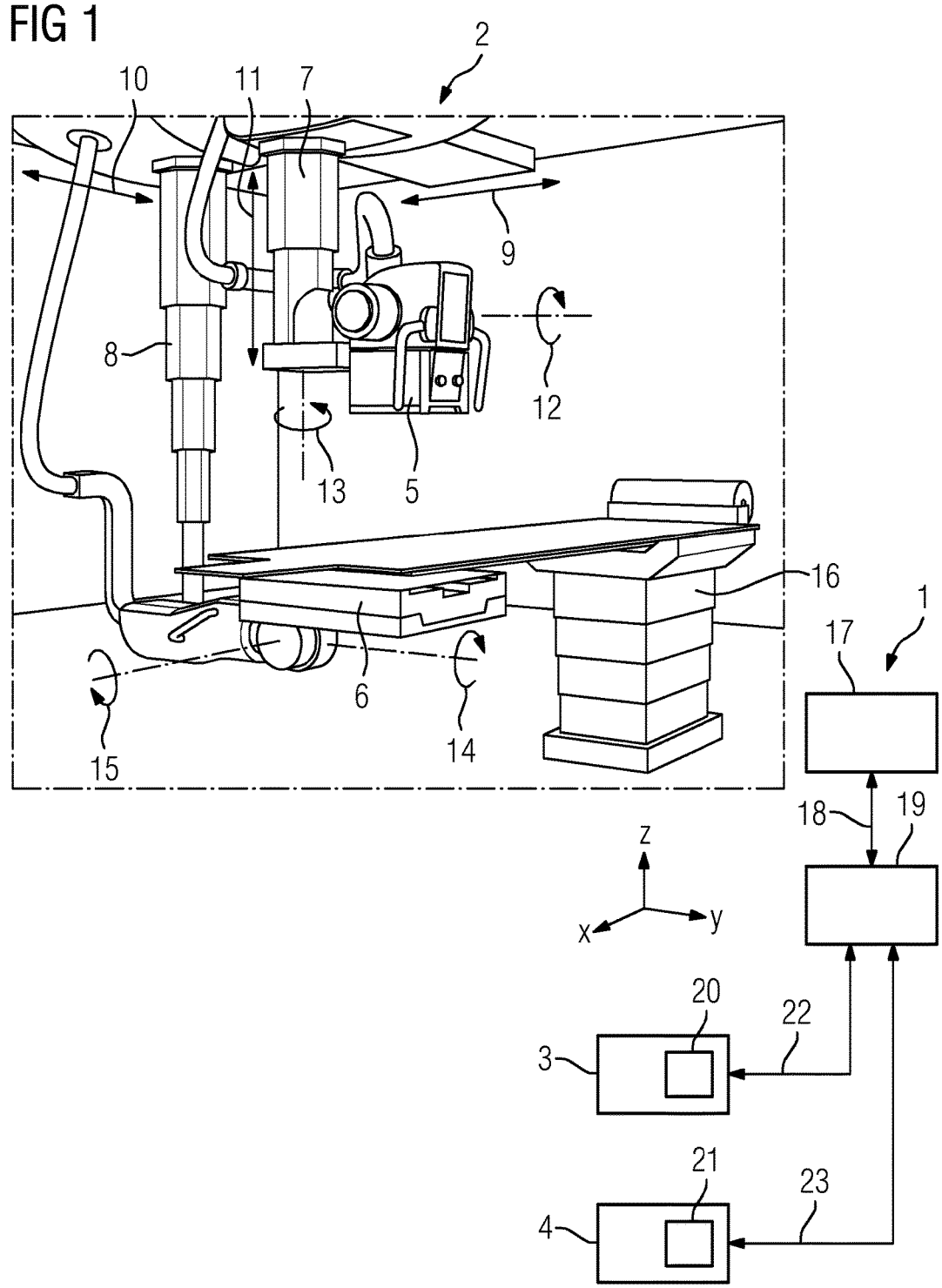
FIG. 1 is a diagrammatic, perspective view of a control system according to the invention.

Referring now to the figures of the drawings in detail and first, particularly to FIG. 1 thereof, there is shown an exemplary embodiment of a control system 1 according to the invention. In the present case, the control system 1 has multiple x-ray devices 2, 3 and 4 of identical design, only the x-ray device 2 of which is shown more exactly for the sake of clarity. The x-ray device 2 has a recording arrangement consisting of an x-ray emitter 5 and an x-ray detector 6, each of which is arranged on robot arms 7, 8, which are implemented separately at least to some extent. By means of different adjusting devices, there are ten degrees of freedom of movement in the x-ray device 2, which are indicated by corresponding arrows 9 to 15. The degrees of freedom of translation indicated by arrows 9, 10 and 11 each apply to both robot arms 7, 8, which means that there are already six degrees of freedom of movement in this case. Arrows 12, 13, 14 and 15 indicate degrees of freedom of movement in rotation. Hence, there are ten resultant degrees of freedom of movement in total, an adjusting device being associated with a degree of freedom of movement in each case.

This multiplicity of ten degrees of freedom of movement allows a wide variety of recording geometries along particular recording trajectories to be set in the x-ray device 2 so as to be able to record projection images from different projection directions, for example, and to ascertain a three-dimensional image data record therefrom as part of a computed tomography reconstruction. In this case, knowledge of the recording geometries of the individual projection images, for example described by projection matrices as geometry parameters, is extremely important in order to obtain high-quality three-dimensional image data records.

In order to ascertain the recording geometries for the various nominal positions and trajectories from which a projection image can be recorded as an x-ray image, a geometry calibration is performed to ascertain calibration parameters, which can also correspond directly to the projection matrices. To this end, a calibration phantom—not depicted in more detail here—is placed on the patient couch or table 16, with scans being performed, for example along the various possible trajectories, that is to say various x-ray images of the calibration phantom are recorded. The nature of the calibration phantom now allows the projection matrix and hence the calibration parameters to be derived directly from the x-ray image of the calibration phantom. On account of mechanical wear and other effects, however, it may arise that the recording geometries alter over time in particular positions along the trajectories, and therefore no longer correspond to the recording geometries described by the calibration parameters. Fresh calibration is then required in order to determine new calibration parameters. The control system 1 depicted here, which is configured for performing the method according to the invention, allows prediction of a suitable time for a fresh calibration and also, if need be, at least in some configurations, a delay in the onset of this time, which will be discussed in more detail below.

The x-ray device 2 contains a controller 17 in which not only is it possible for the calibration parameters to be ascertained and stored during a calibration using an appropriate calibration unit, but also use data from the x-ray device 2 can be captured in an operating phase between two calibrations. In the present case, these use data comprise the number of uses of individual possible trajectories since the last calibration and the total length of movement since the last calibration for each of the ten degrees of freedom of movement. In the case of rotations, the term length of movement naturally also covers angles. Once the time for the fresh calibration has been reached, the controller 17 can also ascertain a piece of difference information that describes how much the calibration parameters of the calibrations delimiting the operating phase differ from one another. The difference information, together with the use data, forms a piece of use information that can be transmitted via a communication link 18, for example containing the Internet, to a central computation device 19, in this case a server, of the control system 1.

Since the x-ray devices 3 and 4 are embodied in an identical design to the x-ray device 2, they also have corresponding controllers 20, 21, which can use appropriate communication links 22, 23 to send use information from various operating phases to the central computation device 19. In this case, the controllers 17, 20, 21 and the central computation device 19 form a control device of the control system 1, which control device is configured for performing the method according to the invention, as will be explained in more detail below with regard to FIG. 2.

Figure 2:
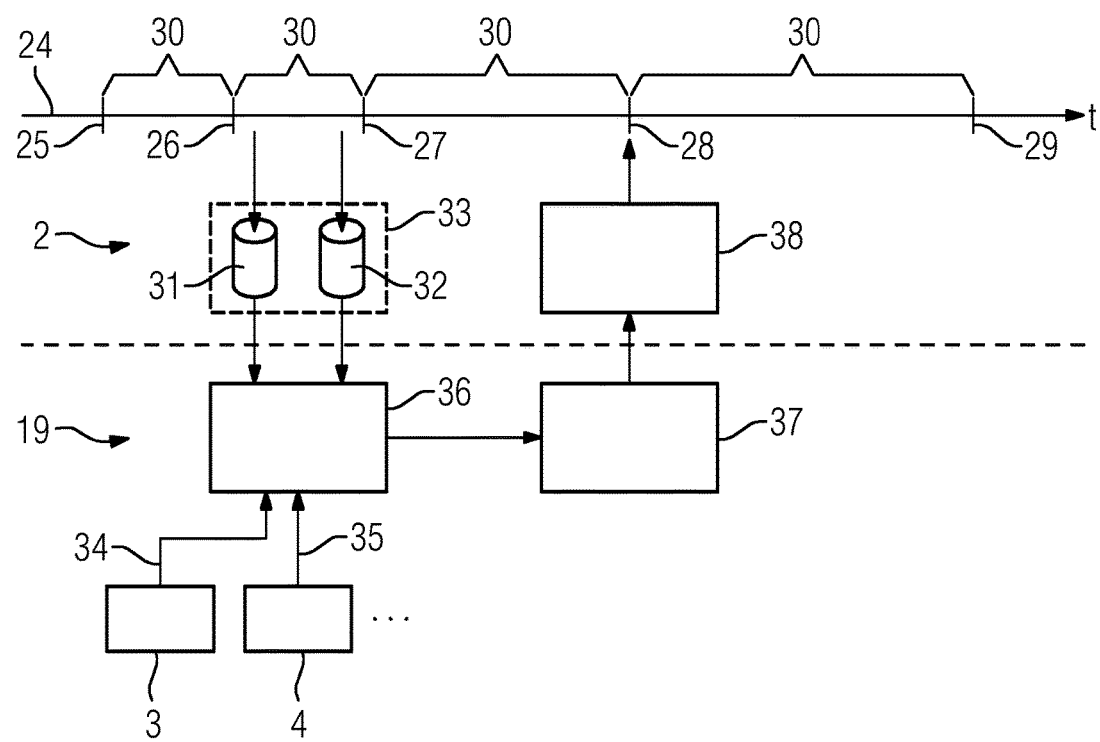
FIG. 2 is a diagram for explaining a method according to the invention.

FIG. 2 first of all contains the depiction of a time axis 24 on which various times 25 to 29 for calibration processes are depicted by way of example. As can be seen, the times 25, 26 and 27 succeed one another at fixed intervals of time, that is to say that the operating phases 30 between them are of equal length. The reason for this is that these calibrations are still in a general data collection phase, since there are still not a sufficient number of sets of use information available on the central computation device 19. That is to say that for the times 25, 26 and 27, the interval between the calibrations is still prescribed, for example as four weeks.

During the operating phases 30 between the calibration times 25-29, the controller 17 of the x-ray device 2, the domain of which is shown in FIG. 2 in a manner separated from the domain of the central computation device 19 by a dashed line, collects the use data 31 and the difference information 32, as described, the difference information being able to be obtained as a sum of the differences in the individual calibration parameters and/or as a sum of the differences in the positions of the individual features of the calibration phantom in the x-ray images during the calibration. Collectively, the use data 31 and the difference information 32 for an operating phase 30 form the use information 33 that is transmitted via the communication link 18 to the central computation device 19. Use information is, as indicated by the arrows 34, 35, also received from the further x-ray devices 3, 4, . . . , which are of identical design. If a number of sets of use information 33 that exceeds a threshold value is available, therefore use information 33 for a number of different operating phases 30 that exceeds the threshold value for example nine, then the use information is used to check whether there is a correlation between the use data 31 and the difference information 32 and hence to ascertain a relationship between the use data and the difference information. This takes place in a step 36.

Since the underlying functional relationship between the use data 31 and the difference information 32 is unknown in this case, a nonparametric multivariate adaptive regression splines method is used as a regression analysis method in the present case, the relationship being modeled mathematically as a weighted sum of basic functions that comprise a constant 1, single hinge functions and products of two or more hinge functions. This model is now trained in order to ascertain the model parameters, in this case the constant weighting coefficients, for example.

The concretized relationship ascertained in this manner is transmitted back in a step 37 to the x-ray devices 2, 3, 4 . . . in order to be used therein to determine, in a step 38, times 28, 29 for fresh calibrations.

Since the use data 31 are captured by the controllers 17, 20, 21 during the operating phases 30 anyway, of course, they can be used to ascertain a piece of predicted difference information using the relationship. This difference information can now be evaluated using a recalibration criterion, with a fresh calibration being performed, by way of example, when a difference value contained in the difference information or computable therefrom exceeds a threshold value.

In the present case, however, there is also an additional functionality, which is not depicted in more detail in FIG. 2 for the sake of clarity. The reason is that the predicted difference information is also used in the present case to perform advance adaptation of the calibration parameters and to exclude particular positions/trajectories of the recording arrangement so as thereby to increase the length of the operating phase 30. In this way, it is therefore possible to postpone the time 28, 29 of a fresh calibration, particularly if particularly movement-intensive trajectories are excluded from use and instead less movement-intensive trajectories are used. Hence, to a certain extent, control of the time 28, 29 of the next, involved calibration is possible.

Although the invention has been illustrated and described in more detail using the preferred exemplary embodiment, the invention is not restricted by the disclosed examples, and other variations can be derived therefrom by a person skilled in the art without departing from the scope of protection of the invention.

The following is a summary list of reference numerals and the corresponding structure used in the above description of the invention:

1 control system
2 x-ray device
3 x-ray device
4 x-ray device
5 x-ray emitter
6 x-ray detector
7 robot arm
8 robot arm
9 arrow
10 arrow
11 arrow
12 arrow
13 arrow
14 arrow
15 arrow
16 patient couch
17 controller
18 communication link
19 computation device
20 controller
21 controller
22 communication link
23 communication link
24 time axis
25 time
26 time
27 time
28 time
29 time
30 operating phase
31 use data
32 difference information
33 use information
34 arrow
35 arrow
36 step
37 step
38 step

The invention claimed is:

1. A method for ascertaining a time for a fresh calibration for ascertaining up-to-date calibration parameters of an x-ray device, the x-ray device having multiple degrees of freedom of movement for a recording configuration containing an x-ray emitter and an x-ray detector, which comprises the steps of:

recording x-ray images of a calibration phantom for at least some of possible recording positions of the recording configuration;

evaluating the x-ray images to ascertain calibration parameters allowing ascertainment of geometry parameters, describing a recording geometry, from position data of the recording configuration being based on the degrees of freedom of movement;

ascertaining in multiple operating phases, situated between two calibrations, of at least one further x-ray device of identical design to the x-ray device, a piece of use information containing use data describing an accumulated use of the degrees of freedom of movement during an operating phase and a piece of difference information describing a difference in the calibration parameters between the calibrations delimiting the operating phase; and determining the time for the fresh calibration from a relationship, determined by collective evaluation of all the use information, between the use data and the difference information on a basis of the use data recorded since a last calibration.

2. The method according to claim 1, which further comprises determining the time on the basis of the use information only when the use information is available for a number of the operating phases for the or all of the x-ray devices that exceeds a threshold value, wherein fixed intervals of time are used beforehand for spacing the calibrations.

3. The method according to claim 1, which further comprises:
recording the use data in a manner resolved according to the degrees of freedom of movement and/or trajectories used for the recording configuration; and/or
ascertaining the difference information as a sum of absolute values of differences based on individual features of the calibration phantom.

4. The method according to claim 3, wherein the use data used are a length of movement along each degree of freedom of movement, and/or the use data based on the trajectories are taken into consideration in a manner weighted with the length of movement along all the degrees of freedom of movement, and/or the trajectories have associated degrees of freedom of movement information, so that the use data based on the degrees of freedom of movement are derived from the use data based on the trajectories.

5. The method according to claim 1, wherein a collection of the use information for multiple x-ray devices involves the use information being transmitted from the x-ray device recording it to a central computation device, where at least part of the evaluating is performed.

6. The method according to claim 1, which further comprises updating the relationship whenever there is a new piece of use information available.

7. The method according to claim 1, which further comprises ascertaining the relationship by virtue of training of a mathematical model described by at least one model parameter.

8. The method according to claim 7, which further comprises ascertaining the relationship by virtue of a nonparametric multivariate adaptive regression splines method.

9. The method according to claim 1, which further comprises ascertaining the time by using the relationship to ascertain a piece of predicted difference information from the use data recorded since a last calibration and evaluating the predicted difference information using a recalibration criterion.

10. The method according to claim 1, wherein in a case of a piece of difference information being broken down according to different differences, a piece of predicted difference information ascertained by means of the relationship from the use data recorded since a last calibration is used for plausibilizing the relationship in an event of the fresh calibration and/or for preadaptation of the calibration parameters and/or restriction of a selection of positions and/or trajectories of the recording configuration before the fresh calibration, namely the fresh calibration shifted to a later time.

11. The method according to claim 1, which further comprises ascertaining the relationship by virtue of training of a mathematical model described by at least one model parameter, namely by virtue of a fit process.

12. A control system for at least one x-ray device, the control system comprising:
a further x-ray device; and
a control device configured for performing a method for ascertaining a time for a fresh calibration for ascertaining up-to-date calibration parameters of the x-ray device, the x-ray device having multiple degrees of freedom of movement for a recording configuration containing an x-ray emitter and an x-ray detector, the method comprises the steps of:
recording x-ray images of a calibration phantom for at least some of possible recording positions of the recording configuration;
evaluating the x-ray images to ascertain calibration parameters allowing ascertainment of geometry parameters, describing a recording geometry, from position data of the recording configuration being based on the degrees of freedom of movement;
ascertaining in multiple operating phases, situated between two calibrations, of the at least one further x-ray device of identical design to the x-ray device, a piece of use information containing use data describing an accumulated use of the degrees of freedom of movement during an operating phase and a piece of difference information describing a difference in the calibration parameters between the calibrations delimiting the operating phase; and
determining the time for the fresh calibration from a relationship, determined by collective evaluation of all the use information, between the use data and the difference information on a basis of the use data recorded since a last calibration.

13. A non-transitory computer medium carrying computer executable instructions to be executed on a processor, the computer executable instructions programmed to perform a method according to claim 1.

* * * * *